(12) United States Patent
Huegerich

(10) Patent No.: US 12,151,111 B2
(45) Date of Patent: Nov. 26, 2024

(54) BODY AREA NETWORK COMMUNICATION COLLISION AVOIDANCE CONCEPT FOR MEDICAL SYSTEMS

(71) Applicant: BIOTRONIK SE & Co. KG, Berlin (DE)

(72) Inventor: Burkhard Huegerich, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 709 days.

(21) Appl. No.: 17/299,673

(22) PCT Filed: Sep. 18, 2019

(86) PCT No.: PCT/EP2019/074968
§ 371 (c)(1),
(2) Date: Jun. 3, 2021

(87) PCT Pub. No.: WO2020/126132
PCT Pub. Date: Jun. 25, 2020

(65) Prior Publication Data
US 2022/0032051 A1 Feb. 3, 2022

Related U.S. Application Data

(60) Provisional application No. 62/780,952, filed on Dec. 18, 2018.

(30) Foreign Application Priority Data

Jan. 18, 2019 (EP) ..................................... 19152531

(51) Int. Cl.
*A61N 1/368* (2006.01)
*A61N 1/05* (2006.01)
(Continued)

(52) U.S. Cl.
CPC .............. *A61N 1/368* (2013.01); *A61N 1/056* (2013.01); *H04L 5/14* (2013.01); *H04W 4/80* (2018.02); *H04L 67/12* (2013.01)

(58) Field of Classification Search
CPC ......... A61N 1/368; A61N 1/056; H04W 4/80; H04L 5/14; H04L 67/12
See application file for complete search history.

(56) References Cited

U.S. PATENT DOCUMENTS

| | | | | |
|---|---|---|---|---|
| 2009/0058635 A1* | 3/2009 | LaLonde | ............... | H04W 12/50 340/539.11 |
| 2009/0063187 A1* | 3/2009 | Johnson | .................. | H04L 67/52 705/2 |

(Continued)

FOREIGN PATENT DOCUMENTS

| | | | | |
|---|---|---|---|---|
| WO | WO-2007047681 A2 * | 4/2007 | ............. | A61N 1/056 |
| WO | WO-2017087642 A1 * | 5/2017 | ........... | A61B 5/0015 |

OTHER PUBLICATIONS

International Search Report (PCT/ISA/210) and Written Opinion (PCT/ISA/237) mailed on Jan. 8, 2020, by the European Patent Office as the International Searching Authority for International Application No. PCT/EP2019/074968.

(Continued)

*Primary Examiner* — Jael M Ulysse
(74) *Attorney, Agent, or Firm* — Buchanan Ingersoll & Rooney PC

(57) ABSTRACT

A medical system, comprising a plurality of devices forming nodes of a network, each device of said plurality of devices is configured to communicate with another device in a wireless fashion by receiving a message from another device in the network or by transmitting a message to another device in the network. A priority is assigned to each device, wherein as long as no other transmission of a message is ongoing in the network, each device is configured to initiate (Continued)

a transmission of a message by transmitting a start signal, wherein the higher the priority of the respective device, the higher the duration of the start signal allocated to the respective device. In case several devices in the network simultaneously initiate a transmission of a message by transmitting a start signal, a permission to transmit a message is automatically granted to the device in the network with the highest priority.

17 Claims, 1 Drawing Sheet

(51) Int. Cl.
*H04L 5/14* (2006.01)
*H04W 4/80* (2018.01)
*H04L 67/12* (2022.01)

(56) References Cited

U.S. PATENT DOCUMENTS

| | | | | |
|---|---|---|---|---|
| 2010/0268304 | A1* | 10/2010 | Matos | G16H 40/63 607/60 |
| 2011/0182223 | A1* | 7/2011 | Patel | H04L 61/5038 370/311 |
| 2012/0082036 | A1* | 4/2012 | Abedi | H04W 84/18 370/329 |
| 2012/0092155 | A1* | 4/2012 | Abedi | H04W 76/50 340/539.12 |
| 2012/0119902 | A1* | 5/2012 | Patro | H04W 52/0238 340/502 |
| 2014/0295858 | A1* | 10/2014 | Li | H04W 48/06 455/450 |
| 2014/0300490 | A1* | 10/2014 | Kotz | A61B 5/7267 340/870.3 |
| 2014/0369268 | A1* | 12/2014 | Huang | G16H 40/67 370/329 |
| 2014/0369339 | A1* | 12/2014 | Nekoui | H04W 72/0446 370/348 |
| 2016/0121128 | A1* | 5/2016 | Fishler | H04W 52/04 607/32 |
| 2016/0183285 | A1* | 6/2016 | Matsuo | H04W 72/52 370/329 |
| 2017/0005911 | A1* | 1/2017 | Kasargod | H04L 45/42 |
| 2017/0143267 | A1* | 5/2017 | Kovacs | A61B 5/742 |
| 2017/0146385 | A1* | 5/2017 | Kovacs | G01G 19/50 |
| 2017/0181645 | A1* | 6/2017 | Mahalingam | G16H 10/60 |
| 2017/0312530 | A1* | 11/2017 | Schilling | A61B 5/0031 |
| 2018/0241488 | A1* | 8/2018 | Daoura | H04W 4/70 |
| 2019/0125361 | A1* | 5/2019 | Shelton, IV | A61B 17/1227 |
| 2019/0160290 | A1* | 5/2019 | Roberts | A61N 1/36507 |
| 2019/0160292 | A1* | 5/2019 | Peichel | A61N 1/3956 |
| 2019/0160293 | A1* | 5/2019 | Reinke | A61N 1/3756 |
| 2023/0146947 | A1* | 5/2023 | Shelton, IV | A61B 17/1285 606/144 |

OTHER PUBLICATIONS

Slama, et al., "A Free Collision and Distributed Slot Assignment Algorithm for Wireless Sensor Networks", 2008 IEEE Global Telecommunications Conference, Nov. 2008, pp. 1-6.

Wong, et al., "On Alleviating Starvation in Wireless Sensor Networks", 2011 IEEE International Conference on Communications, Jun. 2011, pp. 1-5.

* cited by examiner

BODY AREA NETWORK COMMUNICATION COLLISION AVOIDANCE CONCEPT FOR MEDICAL SYSTEMS

CROSS-REFERENCE TO RELATED APPLICATIONS

This application is the United States national phase under 35 U.S.C. § 371 of PCT International Patent Application No. PCT/EP2019/074968, filed on Sep. 18, 2019, which claims the benefit of European Patent Application No. 19152531.0, filed on Jan. 18, 2019, and U.S. Patent Application No. 62/780,952, filed on Dec. 18, 2018, the disclosures of which are hereby incorporated by reference herein in their entireties.

TECHNICAL FIELD

The present invention relates to a medical system utilizing a network, particularly a body are network (BAN).

BACKGROUND

In the framework of the present invention, a body area network (BAN), is a network of devices capable of performing wireless communication within a body area of a patient. The respective device can be an implantable device that is positioned inside the patient's body or a device positioned outside the patient's body. A device positioned outside the person's body may be configured to be worn by the patient and may be arranged on the person's body. The devices of the BAN may communicate wirelessly (particularly short-range) by utilizing suitable communication methods such as methods based on radio waves (radio communication), oscillating electric and/or magnetic fields or ultrasound. Particularly, IEEE 802.15 formally defines a BAN as a communication standard optimized for low power devices and operation on, in or around the human body (but not limited to humans) to serve a variety of applications including medical, consumer electronics/personal entertainment and other.

In a network or BAN working in half-duplex mode, two parties (e.g. devices) can communicate with each other, but not simultaneously (i.e. the communication is one direction at a time). In case such a network/BAN shall be used for the communication between (e.g. implantable) medical devices, it needs to facilitate the exchange of information in a reliable and timely fashion.

The communication between devices can be made reliable by implementing a transmit/response scheme where the transmitting party repeats the transmission until it receives an acknowledging response from the addressed party.

Existing solutions do not handle time critical communication in a reliable timely manner. Half duplex body area networks such as envisioned for the communication between implantable medical devices may need the ability to prevent the collision of transmissions from separate devices when started accidentally at the same time. The collision of the transmission of information may or may not be critical.

If the information to be transmitted is not time critical, the transmission can be made reliable by implementing the transmit/response scheme where the transmitting party repeats the transmission until it receives an acknowledging response from the addressed party. If the information to be transmitted by one device is time critical for another device such as in the synchronization of intra-cardiac pacemaker activities implanted in different heart chambers, the repeated transmission until an acknowledging response is observed may not be sufficient. Time critical information needs a communication concept that prevents the potential collision of transmissions.

The present disclosure is directed toward overcoming one or more of the above-mentioned problems, though not necessarily limited to embodiments that do.

SUMMARY

Therefore, it is an objective to provide a medical system comprising communication concept that prevents the collision of transmissions in a network, particularly in case the network (e.g. BAN) operates in half duplex mode.

A medical system having the features of claim 1 and a method with the features of claim 13 are provided. Further embodiments are stated in the dependent claims.

In one aspect, a medical system is disclosed which comprises a plurality of devices forming nodes of a network provided by the medical system, wherein each device of said plurality of devices is configured to communicate with another device of said plurality of devices via the network in a wireless fashion by receiving a message from another device in the network or by transmitting a message to another device in the network, and wherein a priority is assigned to each device, wherein as long as no other transmission of a message is ongoing in the network, each device is configured to initiate a transmission of a message by transmitting a start signal, wherein the higher the priority of the respective device, the higher the duration of the start signal allocated to the respective device, and wherein in case several devices in the network simultaneously initiate a transmission of a message by transmitting a start signal, a permission to transmit a message is automatically granted to the device in the network with the highest priority.

In another aspect, a method for wireless communication between devices of a medical system is provided, wherein the devices form nodes of a network, and wherein the method comprises the steps of:
  assigning a priority to each device,
  allowing each device in the network to initiate a transmission of a message by transmitting a start signal as long as no other transmission of a message is ongoing in the network, wherein the higher the priority of the respective device, the higher a duration of the start signal allocated to the respective device, and
  in case several devices in the network simultaneously initiate a transmission by transmitting a start signal, granting a permission to transmit a message to the device in the network having the highest priority.

The disclosure thus provides a novel concept to prevent communication collisions in networks such as body area networks, particularly in case the network/BAN comprises half duplex communication.

According to an embodiment, the network is a body area network (BAN) (e.g. as defined above).

Furthermore, according to an embodiment of the system, wherein the devices are configured to communicate with one another via the network in half-duplex mode.

Further, according to an embodiment, each device is configured to be in a receiving mode in which the respective device is able to receive a message from another device and is able to transmit a message of its own and is not inhibited by an ongoing or initiated message of another device of the network. Start sending a start signal might be inhibited by an already ongoing start signal or a message from another device.

Furthermore, according to an embodiment of the system, the respective device is configured to return into the receiving mode for a pre-defined time period after having transmitted a start signal, wherein in case the respective device receives a start signal from another device during this time period, the respective device is configured to postpone transmission of its own message until the ongoing transmission of the start signal from the other device ends, and wherein the respective device is configured to transmit its own message in case the respective device sees no ongoing transmission of a start signal from a different device after its own start signal has ended.

Further, according to an embodiment of the system, no two devices of the network comprise the same start signal duration.

Furthermore, in an embodiment, a difference between the durations of each two start signals is larger than a transition time from transmission to receiving mode of a device among the plurality of devices that comprises the longest transition time.

Furthermore, according to an embodiment of the system, the plurality of devices comprises at least a first and a second medical device, wherein particularly the first device is an implantable medical device, and wherein particularly the second medical device is an implantable medical device.

Furthermore, according to an embodiment, the first device is an implantable intracardiac pacemaker that is configured to be implanted in the heart of a patient. Further, according to an embodiment, the second device is an implantable intracardiac pacemaker that is configured to be implanted in the heart of a patient. Alternatively, the second device can be a sensor. The sensor may be configured to measure a blood pressure of a patient or the sensor can be a loop recorder configured to measure an ECG.

Particularly, the first device is an intracardiac pacemaker configured to be implanted in the right ventricle of the patient. Furthermore, particularly, in case the second device is an intracardiac pacemaker, the latter is preferably configured to be implanted in the right atrium, in the left atrium or in the left ventricle of the patient.

According to a further embodiment, the plurality of devices further comprises a third medical device, wherein particularly the third medical device is an implantable medical device. The third medical device can be an intracardiac pacemaker, the latter may be configured to be implanted in the right atrium, in the left atrium or in the left ventricle of the patient. Also, the third medical device may be a sensor (e.g. configured to measure a blood pressure of a patient) or a loop recorder.

The plurality of devices may also comprise more than three medical devices.

Furthermore, in an embodiment of the method, the method comprises the further step of sending the message from the device having the highest priority and receiving the message by another device in the network in half-duplex mode.

Further, according to an embodiment of the method, the method comprises the further step of maintaining each device in the network in a receiving mode in which the respective device is able to receive a transmission of a message from another device and is able to transmit a message of its own and is not inhibited by an ongoing or initiated message of another device of the network.

Furthermore, according to an embodiment of the method, the method comprises the further steps of prompting the respective device to return into the receiving mode for a pre-defined time period after having transmitted a start signal, and postponing a transmission of a message of the respective device when the respective device sees a start signal from another device during this time period, and allowing the respective device to transmit its own message in case the respective device sees no ongoing transmission of a start signal from a different device after its own start signal has ended.

Furthermore, according to an embodiment of the method, no two devices of the network comprise the same start signal duration. Particularly, a difference between the durations of each two start signals is larger than a transition time from transmission to receiving mode of a device among the plurality of devices that comprises the longest transition time.

Particularly, the method according to the present disclosure can be conducted with the first device, second device, and particularly third device described above. All features disclosed herein with regard to the system can be applied to the method and vice versa.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

In the following, embodiments, features and advantages of the present invention shall be described with reference to the Figures, wherein.

DETAILED DESCIPTION

Figure 2:
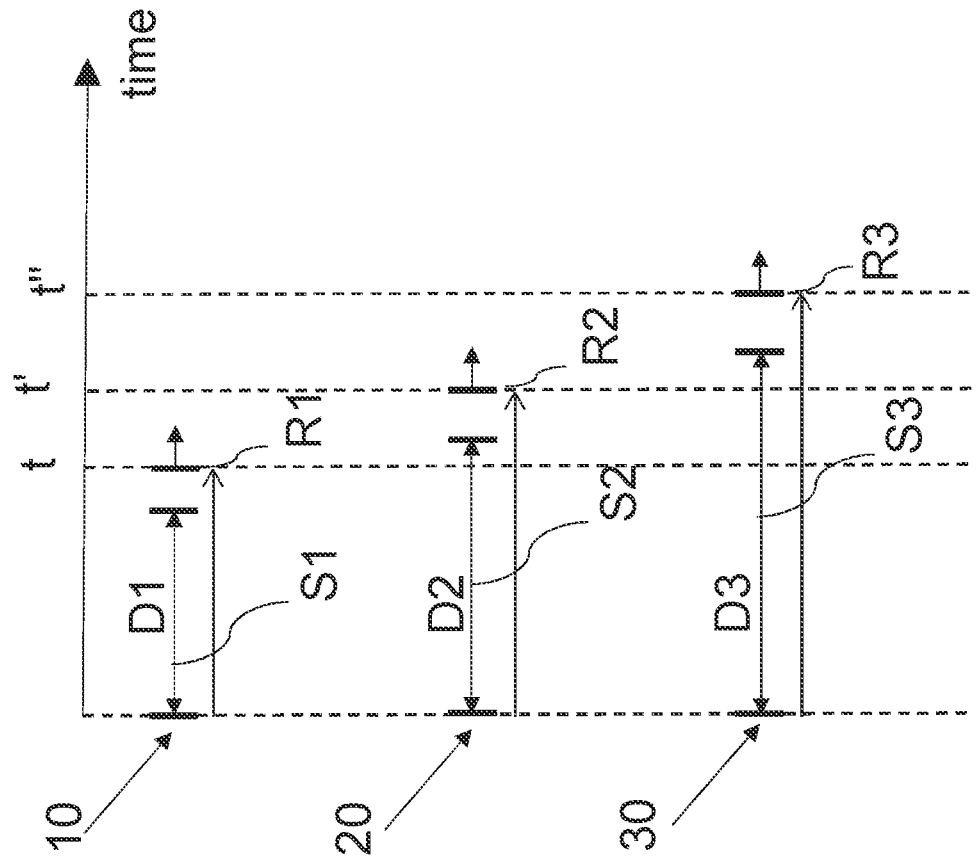
FIG. 2 shows a schematical illustration of transmitting a message in the medical system shown in FIG. 1.
Figure 1:
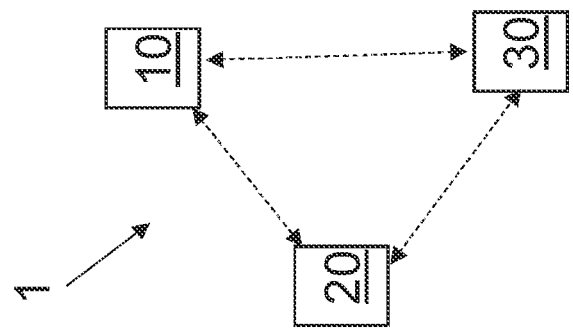
FIG. 1 shows a schematical illustration of an embodiment of a medical system comprising medical devices forming nodes of a network, particularly of a BAN.

FIG. 1 shows in conjunction with FIG. 2 an embodiment of a medical system 1 which comprises at least a first and a second device 10, 20.

Particularly, in an embodiment, the first device 10 can be an intracardiac pacemaker implanted in the right ventricle of a patient, wherein the second device can be an intracardiac pacemaker implanted in the right atrium of the patient. According to another example, the first device 10 can be an intracardiac pacemaker implanted in the right ventricle, and the second device can be an intracardiac pacemaker implanted in the left ventricle. Furthermore, according to an alternative example, the first device can be an intracardiac pacemaker implanted in the right ventricle, whereas the second device 20 can be a sensor, e.g. configured to measure blood pressure of the patient.

In the following, for describing the communication among the devices in a medical system 1, a third device 30 is considered forming a node of the network, too.

Particularly, for enabling communication e.g. in the medical system 1/network shown in FIG. 1, preferably a physical layer is defined to determine the beginning of a data transmission, e.g. in form of a start signal S1, S2, S3 as well as a signal pattern to define the logical bit values of the actual digital data transmission which is denoted as a message herein. Particularly, the communication is based on the duration D1, D2, D3 of the start signal S1, S2, S3 to be dependent on a priority scheme assigned to all the devices 10, 20, 30 communicating within the same network, which particularly is a BAN.

Any device 10, 20, 30 that takes part in the information exchange within the same network/BAN needs to be always in the message receiving mode R1, R2, R3 unless it is granted permission to transmit its own message. After transmitting, the device 10, 20, 30 preferably needs to return to the receiving mode R1, R2, R3 as soon as possible.

As long as no other transmission is ongoing any device 10, 20, 30 may initiate a transmission by transmitting a start signal S1, S2, S3. The duration D1, D2, D3 of the start signal S1, S2, S3 for each device 10, 20, 30 is dependent on the priority assigned to the device 10, 20, 30. By starting to transmit a start signal S1, S2, S3 the device 10, 20, 30 indicates the intention to transmit information (i.e. a message).

After transmitting the start signal S1, S2, S3 the transmitting device 10, 20, 30 needs to first return into receiving mode R1, R2, R3 for a limited amount of time. If at this time the device 10, 20, 30 sees an incoming transmission (receiving an ongoing start signal from a different device), the device 10, 20, 30 needs to postpone its own message transmission until the ongoing message/start signal transmission stops. If the device 10, 20, 30 sees no ongoing transmission of a start signal S1, S2, S3 from a different device 10, 20, 30 after its own start signal S1, S2, S3 ended, the device 10, 20, 30 is allowed to transmit its information.

If several devices 10, 20, 30 initiate simultaneously the transmission of the start signal S1, S2, S3, a situation that is shown in FIG. 2, the permission to send is granted automatically to the device with the higher priority by the proposed implementation of the start signal S1, S2, S3. The priority scheme assigned to each device 10, 20, 30 within the same network (e.g. BAN) defines the duration D1, D2, D3 of the allowed transmission of the start signal S1, S2, S3. The device 30 with the highest priority is allocated the longest duration of the start signal D3 and the device 10 with the lowest priority is allocated the shortest duration D1 of the start signal S1. Preferably, no two devices 10, 20, 30 must have the same start signal duration D1, D2, D3 assigned if working in the same network, e.g. BAN. The incremental differences in the start signal duration D1, D2, D3 needs to be longer than the transition time from transmission to receiving of the device 10, 20, 30 with the longest transition time to ensure that each device 10, 20, 30 will be able to see the ongoing start signal of a higher priority device.

Particularly, as shown in FIG. 2 as an example, the first device 10 comprises the lowest priority (and consequently shortest start signal duration D1) and the third device 30 the highest priority (longest start signal duration D3), wherein the second device 20 comprises a priority in between the lowest and highest priority (duration D2 between D1 and D3). All three devices 10, 20, 30 initiate the transmission of their respective start signal S1, S2, S3 at the same time to request the transmission of a message, respectively.

The first device 10 comprises the lowest priority and therefore returns to the receiving mode R1 at time t first, wherein the first device 10 then sees the incoming start signals S2, S3 from the higher priority second and third devices 20, 30 and therefore postpones transmission of its message to wait for the incoming messages.

Furthermore, the second device 20 returns to the receiving mode R1 after the first device 10 at time t' and then sees an incoming start signal S3 from the higher priority third device 30. Consequently, the second device 20 postpones its transmission of a message and waits for the incoming message of the third device 30.

Finally, the highest priority third device 30, after having transmitted its start signal S3, returns to the receiving mode R3 after the other two devices 10, 20 at time t" and therefore sees no incoming start signals S1, S2. Therefore, the third device 30 is automatically allowed to start transmission of its message.

Particularly, one advantage of the present disclosure may be the ability to avoid lengthy arbitration schemes in order to prevent the loss of information due to information transmission collisions in a network, particularly in a body area network (BAN), operating e.g. in the half duplex mode.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:
1. A medical system, comprising:
    a plurality of devices forming nodes of a network;
    wherein:
        each device of said plurality of devices is configured to communicate with another device of the network in a wireless fashion by receiving a message from another device in the network or by transmitting a message to another device in the network,
        a priority is assigned to each device,
        as long as no other transmission of a message is ongoing in the network, each device is configured to initiate a transmission of a message by transmitting a start signal, the start signal having a duration based on the device's assigned priority, and
        when several devices in the network simultaneously initiate a transmission of a message by transmitting a start signal, a permission to transmit a message is automatically granted to a transmission-initiating device in the network having a highest priority.
2. The medical system according to claim 1, wherein the network is a body area network.
3. The medical system according to claim 1, wherein each device is configured to communicate with another device in half-duplex mode.
4. The medical system according to claim 1, wherein:
    each device is configured to be in a receiving mode,
    when in receiving mode, a receiving-mode device is able to:
        receive a message from another device,
        transmit a message of its own, and
        not be inhibited by an ongoing or initiated message of another device of the network.
5. The medical system according to claim 4, wherein:
    the receiving-mode device, after having transmitted a start signal, is configured to return into the receiving mode for a pre-defined time period,
    when the receiving-mode device detects an ongoing transmission of a start signal from another device during the pre-defined time period, the receiving-mode device is configured to postpone transmission of a message from the receiving-mode device until the ongoing transmission of the start signal ends, and when the receiving-mode device detects absence of an ongoing transmission of a start signal from another device during the pre-defined time period, the receiving-mode device is configured to transmit a message after its start signal ends.

6. The medical system according to claim 1, wherein the start signal duration for each device differs from the start signal duration for another device.

7. The medical system according to claim 1, wherein a difference between the durations of each two start signals is larger than a transition time from transmission to receiving mode of a device among the plurality of devices that comprises a longest transition time.

8. The medical system according to claim 1, wherein the plurality of devices comprises at least a first medical device and a second medical device.

9. The medical system according to claim 8, wherein the first medical device is an intracardiac pacemaker, and/or wherein the second medical device is an intracardiac pacemaker or a sensor configured to measure a blood pressure of a patient.

10. The medical system according to claim 9, wherein the first medical device is an intracardiac pacemaker configured to be implanted in a right ventricle of the patient.

11. The medical system according to claim 9, wherein the second medical device is an intracardiac pacemaker configured to be implanted in a right atrium or in a left ventricle of the patient.

12. The medical system according to claim 8, wherein the plurality of devices further comprises a third medical device.

13. A method for wireless communication between devices of a medical system, wherein the devices form nodes of a network, and wherein the method comprises the steps of:
    assigning a priority to each device,
    allowing each device in the network to initiate a transmission of a message by transmitting a start signal as long as no other transmission of a message is ongoing in the network, the start signal having a duration based on the device's assigned priority, and
    when several devices in the network simultaneously initiate a transmission by transmitting a start signal, granting a permission to transmit a message to a transmission-initiating device in the network having a highest priority.

14. The method according to claim 13, further comprising allowing each device in the network to operate in a receiving mode, wherein:
    when in receiving mode, a receiving-mode device is able to:
        receive a message from another device,
        transmit a message of its own, and
        not be inhibited by an ongoing or initiated message of another device of the network.

15. The method according to claim 14, further comprising:
    allowing the receiving-mode device, after having transmitted a start signal, to return into the receiving mode for a pre-defined time period,
    when the receiving-mode device detects an ongoing transmission of a start signal from another device during the pre-defined time period, postponing a transmission of a message from the receiving-mode device until the ongoing transmission of the start signal ends, and
    when the receiving-mode device detect absence of an ongoing transmission of a start signal from another device during the pre-defined tie period, allowing the receiving-mode device to transmit a message after its start signal ends.

16. The method according to claim 13, wherein the start signal duration for each device differs from the start signal duration for another device.

17. The method according to claim 13, wherein a difference between the durations of each two start signals is larger than a transition time from transmission to receiving mode of a device among the plurality of devices that comprises a longest transition time.

* * * * *